(12) United States Patent
Doskocil et al.

(10) Patent No.: US 10,874,869 B2
(45) Date of Patent: Dec. 29, 2020

(54) ELECTROSTIMULATION DEVICE

(71) Applicant: Tesla Medical, s.r.o., Ostrava (CZ)

(72) Inventors: Lukas Doskocil, Chocen (CZ); Tomas Vesely, Prague (CZ)

(73) Assignee: Tesla Medical, s.r.o., Ostrava (CZ)

( * ) Notice: Subject to any disclaimer, the term of this patent is extended or adjusted under 35 U.S.C. 154(b) by 207 days.

(21) Appl. No.: 15/742,309

(22) PCT Filed: Jul. 6, 2016

(86) PCT No.: PCT/CZ2016/000074
§ 371 (c)(1),
(2) Date: Jan. 5, 2018

(87) PCT Pub. No.: WO2017/005227
PCT Pub. Date: Jan. 12, 2017

(65) Prior Publication Data
US 2018/0369600 A1   Dec. 27, 2018

(30) Foreign Application Priority Data

Jul. 6, 2015  (CS) ...................................... 2015-467
Jul. 6, 2015  (CS) ...................................... 2015-468

(51) Int. Cl.
*A61N 2/00* (2006.01)
*A61N 1/04* (2006.01)
(Continued)

(52) U.S. Cl.
CPC ........... *A61N 2/002* (2013.01); *A61N 1/0456* (2013.01); *A61N 1/0472* (2013.01);
(Continued)

(58) Field of Classification Search
CPC ...... A61N 2/002; A61N 2/02; A61N 1/36014; A61N 2/006; A61N 1/0472; A61N 2/06; A61N 1/36021; A61N 1/0456
See application file for complete search history.

(56) References Cited

U.S. PATENT DOCUMENTS

| | | |
|---|---|---|
| 4,765,310 A | 8/1988 | Deagle |
| 6,461,288 B1 | 10/2002 | Holcomb |

(Continued)

FOREIGN PATENT DOCUMENTS

| | | |
|---|---|---|
| CN | 1101296 A | 4/1995 |
| DE | 2659115 A1 | 7/1978 |

(Continued)

OTHER PUBLICATIONS

International Search Report received in PCT/CZ2016/000074, dated Oct. 27, 2016.

(Continued)

*Primary Examiner* — Christine H Matthews
*Assistant Examiner* — Joshua Daryl D Lannu
(74) *Attorney, Agent, or Firm* — Suzannah K. Sundby, Esq.; Canady + Lortz LLP

(57) ABSTRACT

The subject of the invention is a device for electrical stimulation of tissue consisting of an electrode and a magnet, which allows to reach deeper located regions without the need for invasive surgery. This helps to achieve therapeutically success in broader range of patients.

18 Claims, 2 Drawing Sheets

(51) Int. Cl.
*A61N 1/36* (2006.01)
*A61N 2/06* (2006.01)
*A61N 2/02* (2006.01)

(52) U.S. Cl.
CPC ..... *A61N 1/36021* (2013.01); *A61N 1/36034* (2017.08); *A61N 2/006* (2013.01); *A61N 2/02* (2013.01); *A61N 2/06* (2013.01)

(56) References Cited

U.S. PATENT DOCUMENTS

| | | |
|---|---|---|
| 2010/0056845 A1 | 3/2010 | Hunter |
| 2013/0184792 A1 | 7/2013 | Simon |

FOREIGN PATENT DOCUMENTS

| | | | |
|---|---|---|---|
| DE | 3930930 C1 | 10/1990 | |
| JP | 2002065867 A | 3/2002 | |
| WO | 1999012605 A1 | 3/1999 | |
| WO | 2002000294 A1 | 1/2002 | |
| WO | 2008103977 A1 | 8/2008 | |
| WO | 2013113297 A1 | 8/2013 | |
| WO | WO-2013113297 A1 * | 8/2013 | ......... A61N 1/36007 |
| WO | 2015063534 A1 | 5/2015 | |

OTHER PUBLICATIONS

Written Opinion received in PCT/CZ2016/000074, dated Oct. 27, 2016.
Supplementary European Search report received in EP16820877.5, dated Jun. 11, 2019.
Transcutaneous electrical nerve stimulation, Wikipedia.org, https://en.wikipedia.org/wiki/Transcutaneous_electrical_nerve_simulation, retrieved Apr. 26, 2020.
Search Report received in CZ Application No. PV2015467 dated Feb. 5, 2016.
Search Report received in CZ Application No. PV2015468 dated Feb. 9, 2016.

* cited by examiner

ELECTROSTIMULATION DEVICE

FIELD OF THE INVENTION

The invention relates to an electrostimulation device, which enables penetration of electric current and magnetic field into a tissue such that there is no simultaneous mechanical damage done to the tissue. This is nowadays used particularly in human medicine for stimulation of nerve fibres.

BACKGROUND OF THE INVENTION

Utilization of electromagnetic field interaction with nerve fibres, as described in documents U.S. Pat. No. 7,857,746 and US20130304159, constitutes the prior art. Electrical neurostimulation has been used for the treatment of pain, urinary incontinence, mental and other difficulties, as well as for the prevention of vascular disease, as disclosed in U.S. Pat. No. 5,358,513. The use thereof is limited by the risk of damage which is always associated with needling of the needle electrodes into close proximity of the nerve, and by the necessity to ensure the ability of the electric field to penetrate to a depth and at the same time with sufficient accuracy to target nerve fibre for non-invasive stimulation of deeper-lying nerve fibres and for non-invasive stimulation of persons with larger layer of fat.

A proposed solution could be the increase of current density up to the upper limit of threshold motoric region. However, this may induce irritation of nociceptive skin receptors, and in case of monophasic current, a gradual change of pH near the negative active electrode caused by electrolysis of interstitial fluid. A big limitation is thus represented by the undesirable effects of electric current on an organism, such as pain at the site of electrode contact, painful muscle contractions, eventually tissue destruction by means of electrolysis.

Not only applying the electric field but also the pressure may be used to stimulate the nerve fibres and for therapy. U.S. Pat. No. 8,187,212 discloses the usage of mechanical pressure on the peroneal nerve in order to reduce back pain and other kinds of pain. Unfortunately, mechanical action, in contrast to electric simulation, cannot be used in most of the applications and it is also very unpleasant for the patient.

Electrodes intended for being attached to a particular body part (head, calf, and the like) or eventually for being inserted into body openings as well as for implementation into tissues by means of wireless connection through the skin are known. The main drawback of electrostimulation is achieving the electric fields crossing the suitable neural pathways which would be strong enough.

There is therefore a need for the electric field to penetrate deeper into the tissue, hit the nerve fibre precisely and cause the required stimulation with minimal side effects. In patent WO2009061142, a common effect of magnetic and electric field is used for treatment of tissues, however, this device is not adapted for repeated and effective hitting of the neural pathway. The solution is provided by the invention described below.

Electrodes for electrostimulation are described in the international patent application WO2013113297. WO2013113297 discloses an electrode for non-invasive electric nerves stimulation and for transcutaneous neurostimulation treatment comprising a magnet and an electrode without skin penetration. Such solution does not provide sufficient penetration of the charged particles to the patient's body.

SUMMARY OF THE INVENTION

The invention is related to electrostimulation device comprising at least one magnet to form a magnetic field, the first pole of the electrode being surrounded by the magnetic field, a fixation element, a source, wiring and the second pole of the electrode, wherein the first electrode pole and the second electrode pole are separated and adapted on one of its sides for electrical connection with the skin, and being connected by means of wiring to the source, characterized in that the magnet is provided with a pole piece for concentrating the flux of charged particles through the tissue into a thin channel. Such solution with a pole piece has a much greater density at the required site of the tissue, and thus ensures sufficient stimulation for all patients, for example, even in case of overweight patients, where a wider layer of subcutaneous fat needs to be penetrated.

In a preferred embodiment is the first electrode pole arranged inside the magnet with an opening or it is surrounded by several magnets. Such solution ensures that the magnetic field is axially symmetric.

In another preferred embodiment, at least one magnet is as an electromagnet. Such solution allows regulation of magnetic field intensity, and in case of more electromagnets, it allows regulation of flow direction of electric current of the tissue.

Preferably, at least two electromagnets may be used to regulate the direction of magnetic field and charged particles using different excitation of the electromagnets.

Preferably, a permanent magnet may be used, which reduces the power requirements.

In a preferred embodiment are the first electrode pole and the second electrode pole spaced at a maximum of 15 cm from each other.

It is advantageous when the first electrode pole and the second electrode pole are tightly connected to each other and thus form one bipolar electrode. Such solution makes it easier to re-stimulate the same place and ensures stable characteristics of the magnetic field. The bipolar electrode thus comprises positive as well as negative electrode pole in one device and it is no longer necessary to attach other electrodes on the skin.

In a preferred embodiment are the first electrode pole and the second electrode pole connected by means of wiring to the source adapted for current setting with values of 0-50 mA.

In another embodiment is the electric current source adapted for frequency settings of 1 to 15 Hz. Such solution is the most preferred one, for example, for treatment of incontinence.

In another preferred embodiment is the source of electric current adapted for frequency settings of 50 to 150 Hz. Such solution is the most preferred one for treatment of pain.

In a preferred embodiment is the source adapted for a supply of alternating current with the option to change the form of the time course. Such solution allows to choose the most effective forms of time course for various applications and various subjects.

In an alternative preferred embodiment, the electrostimulation device comprises at least one main magnet to form the magnetic field and a passive conductive contact to form the electric field, a fixation element, a source and wiring, wherein the passive conductive contact and the main magnet are arranged on the fixation element so that they are isolated from each other. The passive conductive contact is adapted for electrical connection with tissue and it is connected to the source by means of wiring. The main magnet is adapted to electrically connect to the tissue on one of its sides, and by means of wiring it is connected to the source on an opposite potential than the passive conductive conduct. Such device enables the electric current to penetrate to greater depth of the tissue, and it is structurally simpler, which decreases the production costs. Magnetic field of the magnet prevents the dispersion of electric current and thus enables stimulation of deeper located nerves.

In a preferred embodiment is the main magnet on its side facing the skin provided with a diamagnetic wedge, which is arranged so that it is entirely or at least substantially surrounded by the magnetic field from the main magnet, wherein the diamagnetic wedge is made of diamagnetic as well as electrically conductive material, and is adapted for electrical connection with the tissue. Such solution allows the electric current to reach greater depths of the tissue. It is preferred for a broad range of applications described above, among them also for stimulation of nerve fibres. It is also irreplaceable in stimulation of obese patients, as their stimulated points are located under thicker layer of subcutaneous fat.

In another preferred embodiment is the main magnet provided with the pole piece for concentration of the flow of the charged particles through tissues into a thin channel. Such solution allows usage of a slightly weaker magnet and more precise targeting of the desired location.

Preferably, the main magnet is an electromagnet. Such solution provides the same main function as the solution, where the main magnet is a permanent magnet, and moreover, it provides a possibility to regulate the magnetic field.

This may be preferably used in an embodiment, where the main magnet is represented by at least two electromagnets to direct the magnetic field and the charged particles by means of different excitation of these electromagnets. Such solution provides an automatic targeting on, for example, the desired nerve fibre without the necessity to search for the fibre by subsequent replacing of the electrostimulation device, which is time consuming and uncomfortable for the patient.

In another embodiment is the main magnet a permanent one. This solution is suitable especially for its simplicity.

Further according to a preferred embodiment, the main magnet of the electrode and the passive conductive contact of electrode are spaced from each other for maximum of 15 cm.

In another embodiment are the main magnet of the electrode and the passive conductive contact of the electrode firmly attached together and thus form one bipolar electrode. The bipolar electrode thus comprises the positive and the negative electrode pole in one electrode and it is therefore not necessary to attach another electrode on the skin.

According to a preferred embodiment are the main magnet of the electrode and the passive conductive contact of the electrode attached by means of wiring to a source of electric current adapted for the current settings of 0 to 50 mA. Such solution allows the setting of such current, which is the most suitable for the particular patient.

In another embodiment is the source of electric current adapted for the frequency settings of 1 to 15 Hz. Such solution is the most suitable for example for the treatment of incontinence.

In another preferred embodiment is the source of electric current adapted for the frequency settings of 50 to 150 Hz. Such solution is the most preferred one for example for the treatment of pain.

DESCRIPTION OF PREFERRED EMBODIMENTS

Figure 1:
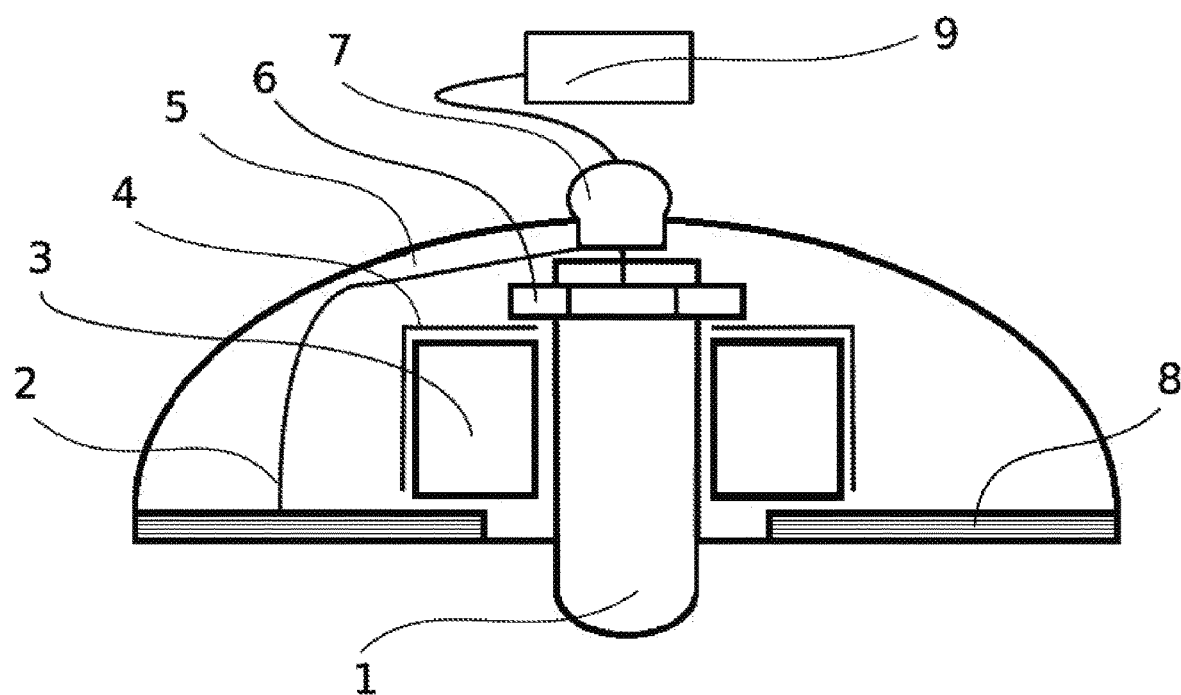
FIG. 1 Schematic illustration of the electrostimulation device with a pole piece.
Figure 2:
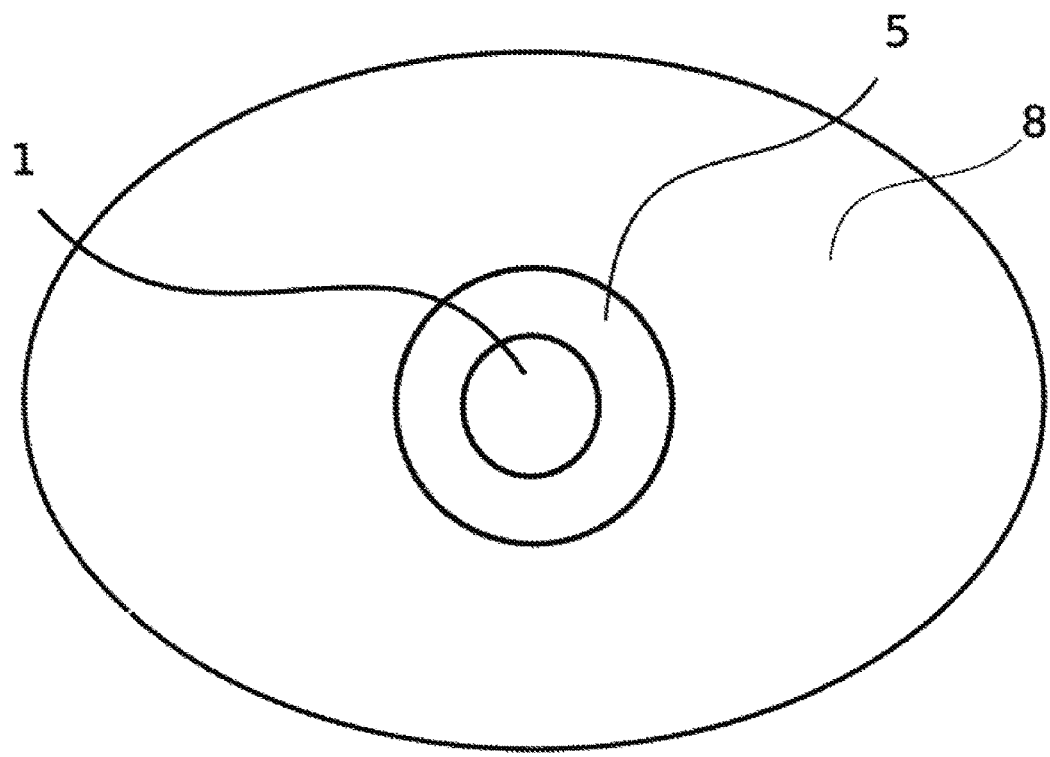
FIG. 2 A view on a part of the electrostimulation device with a pole piece aligned with the skin.

An example of geometric arrangement of the electrostimulation device parts is illustrated in the FIGS. 1 and 2, the said device comprising a magnet 3, a pole piece 4, a first electrode pole 1 and a second electrode pole 8. The magnet 3 serves to increase the depth of penetration with low stimulation currents. Together with the pole piece 4 it is able to linearize and concentrate the parabolic field lines of electric field in an axial direction around the axis of the first electrode pole 1. This creates substantially a tunnel effect for the direction of movement of ions and their concentration, being the carriers of electric charges in intercellular spaces. In this example, the magnet 3 is a permanent one in a hollow cylindrical shape, through the centre of which extends the first electrode pole 1, which is for example made of stainless steel. The first electrode pole 1 is preferably of a round shape in the region which is in contact with the skin, and it is covered with a layer of suitable material, such as silver. The outer coat and the side of the permanent magnet 3 distant from the skin are surrounded by the pole piece 4 made of soft magnetic material. The first electrode pole 1 is on its side, which is distant from the skin, provided with a thread for deployment of a nut 6 and terminated with an adapter 7 for connection of the wiring. The second electrode pole 8 in annular shape is attached to the fixation element 5, wherein it is separated from the first electrode pole 1 by means of a gap, or eventually insulant. It is thus a bipolar electrode, the arrangement of the first electrode pole 1 and the second electrode pole 8 is fixed. The magnet 3 is separated from the first electrode pole 1 by means of insulant, or eventually also an air gap. The north pole of the magnet 3 is oriented toward the tissue. The first electrode pole 1, the magnet 3, the pole piece 4 and the second electrode pole 8 are made of materials intended for medical use, and are electrically isolated from each other, except for the contact region between the magnet and the pole piece. The insulation is also made of material which is suitable for medical use, and which is water resistant and resistant to frequent sterilization.

The magnet 3 may be preferably an electromagnet. In this case, as it is apparent to one skilled in the art, it is possible by means of tuneable excitation to set the form of the region with the highest concentration of the charge carriers, thus a kind of channel. In case several electromagnets are used, it is possible to affect the flow direction of electric current in the tissue by means of different excitation. This may be for example used in search for the desired nerve, even in case of inaccurate placement of electrostimulation device on the skin.

A source 9 of alternative current is connected between the first electrode pole 1 and the second electrode pole 8. It is possible to set the frequency on 1 to 15 Hz and the pulses may be monophasic or biphasic and, for example, rectangular, sinusoidal or triangular, with exponential tapers or decays and with widths from 0.1 to 5 ms with an amplitude from 0 up to 50 mA. The most preferred and very efficient seem to be the frequencies from 4 to 6 Hz.

A harness for fixing the device on the particular place as well as an electric current supply are included. The right arrangement of the electrostimulation electrode is crucial for the method's efficiency as well as for elimination of risk of reduced efficiency of the method resulting from improper manipulation with the electrode. The fixation element 5 provides repeated attachment of the electrode at the same electrostimulating region. A special harness is used to fix the position of the electrode, which is, thanks to its structure, able to use the shape of human body as a fixing point and thus form a shape which is adjusted permanently to the patient and provides the same conditions for each stimulation.

Figure 3:
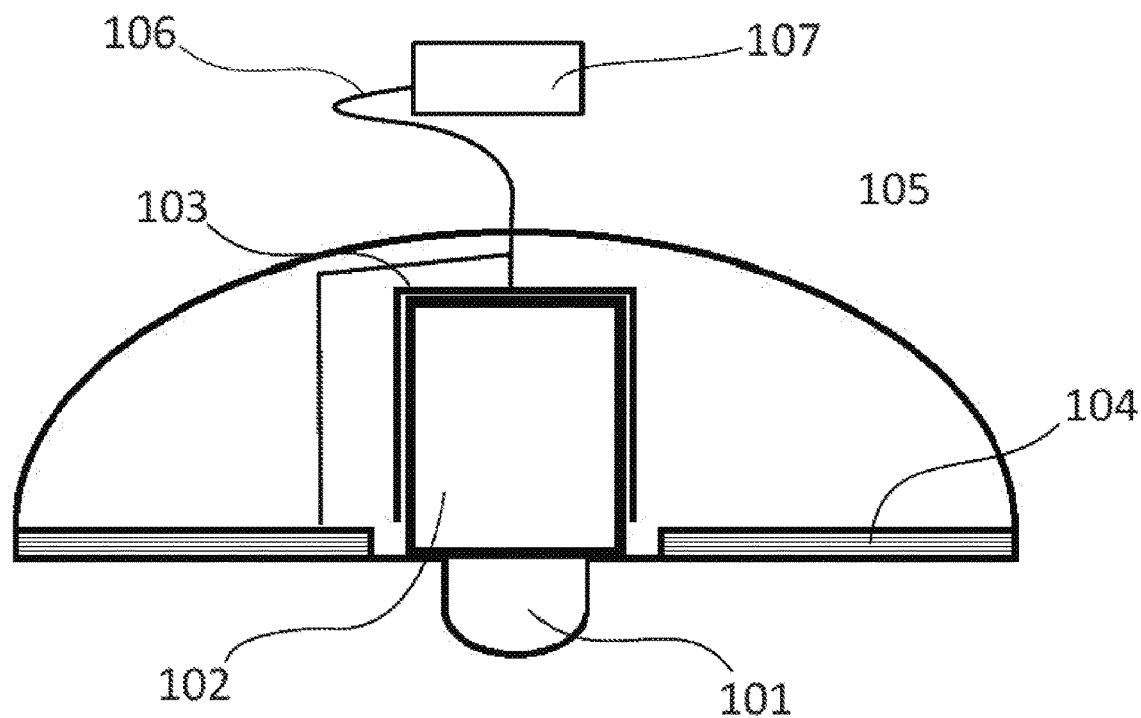
FIG. 3 Schematic illustration of the section of electrostimulation device with a conductive magnet.
Figure 4:
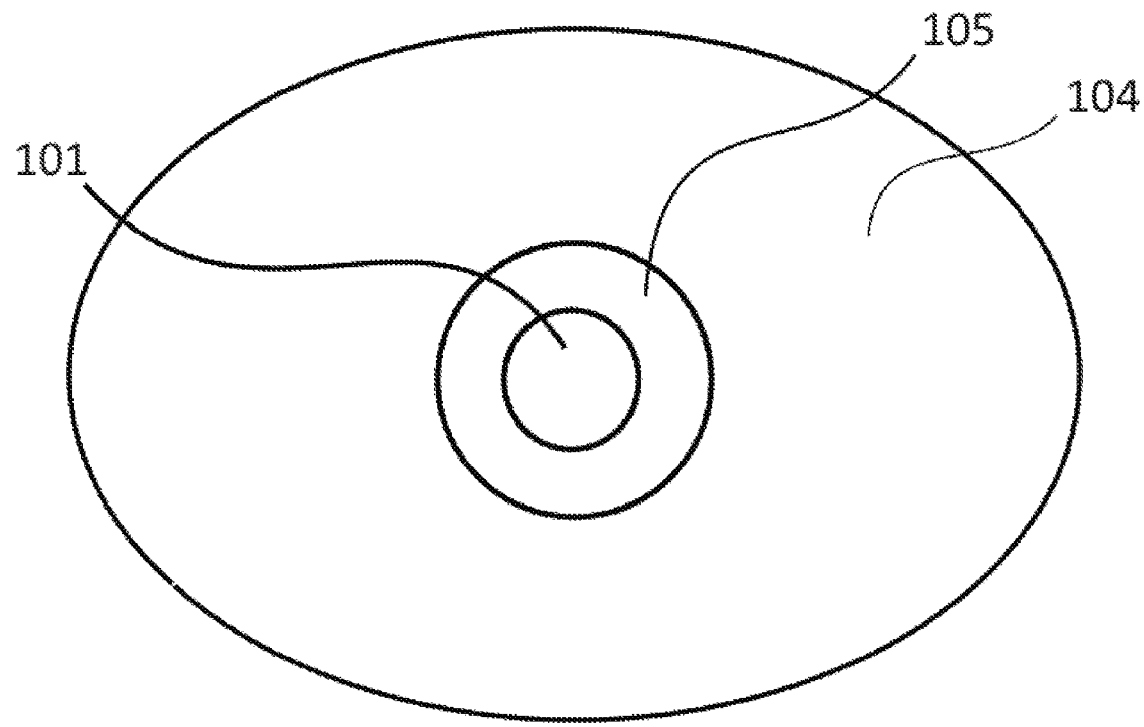
FIG. 4 A view on a part of electrostimulation device with a conductive magnet attached to the skin.

Another exemplary embodiment of geometric arrangement of active parts is the electrostimulation device in the FIGS. 3 and 4, which comprises a diamagnetic wedge 101, a main magnet 102 and a pole piece 103. These increase the depth range of the electric current flowing between the diamagnetic wedge 101 and the passive conductive contact 104 even with low stimulation currents. In this exemplary embodiment, the function of one of the electrode poles is performed by the main magnet 102 and the function of the second electrode pole is performed by the passive conductive contact 104. Thanks to their arrangement they are able to linearize and concentrate the parabolic electric field lines in an axial direction around the axis of the main magnet 102. This creates a channel of ions, limited in its diameter and movement direction of the magnetic pole ions. Ions, being the carriers of electric charges in intercellular spaces thus move along trajectories determined by the magnetic field lines. The diamagnetic wedge 101 performs two functions. It diverts the magnetic field lines from the axis of the main magnet 102 and provides the electrical connection with the skin. In this embodiment is the diamagnetic wedge 101 made of copper and it is of cylindrical shape, which is rounded on its side adjacent to the tissue in order to provide better contact with the skin and the greatest comfort for the patient. As it is apparent from the FIG. 4, the diamagnetic wedge 101 is located so that it is entirely or at least substantially surrounded by the magnetic field from the main magnet 102. In order to perform its function while being well maintained it is further covered with a layer of gold or any other inert and harmless material, which conducts electric current well. The outer housing and the base of the main magnet 102 distant from the skin are, in a preferred embodiment, surrounded by a pole piece 103 made of soft magnetic material. The diamagnetic wedge 101 is on its side distant from the skin connected with the main magnet 102 by means of conductive adhesive or any other conductive connection, and except for the above described effects it also prevents the formation of so called magnetic shirt circuit on the side of the main magnet 102 facing the skin. In this example, the passive conductive contact 104 of the electrode is represented by a thin sheet of copper, which may be gold plated, it is possible to use other diamagnetic materials, such as silver, gold, bismuth, and electrically conductive plastics with various compositions. In the figures is the passive conductive contact 104 of the electrode made in annular shape and it is attached to the fixation element 105, wherein it is separated from the main magnet 102 by means of a gap, which is filled with insulant, from which the fixation element 105 is made. However, in other embodiments, the passive conductive contact 104 may be made using various types of conductive fabrics, or eventually one of the conductive gels commonly used in medicine, or any other conductive material, may be used with application. In this example, the main magnet 102 is a neodymium one (NdFeB). The main magnet 102 is formed by one, or in other embodiments by several, magnets arranged next to each other and its north pole is facing the skin. The fixation element 105 and the passive conductive contact 104 of the electrode are made of materials intended for medical use, which are water resistant and resistant to frequent sterilization.

The main magnet 102 is preferably an electromagnet. In this case it is possible using the suitable source to set the form of the region with the highest concentration of charged carriers, thus a kind of channel, by means of tuneable excitation, as it is apparent to one skilled in the art. Moreover, in case the main magnet 102 is represented by several electromagnets, it is possible to direct the flow direction of the electric current in the tissue by means of different excitation. This can, for example, be used for finding the desired nerve, even in case of inaccurate placement of the electrostimulation device on the skin.

A source 107 of electric power is connected between the diamagnetic wedge 101 and the passive conductive contact 104 of the device. The form as well as the signal frequency of its output may be adjusted. Preferably, it is possible to use frequencies from 0.1 to 100 Hz, and the impulses may be monophasic, biphasic, as well as rectangular, sinusoidal and triangular in their shape, with exponential tapers of decays, and with the widths from 0.1 to 5 ms with the amplitude from 0 up to 50 mA. The most preferred and efficient frequencies seem to be 1 to 15 Hz, however, each patient may respond optimally to any other frequency, so the individual settings play an important role.

The fixation element 105 for fixing the device at the particular region and for electric current supply is included. The proper placement of the electrostimulating electrode is crucial for the efficiency of the whole method as well as for eliminating the risk of reduced efficiency resulting from improper manipulation with the electrode. The fixation element 105 provides the repeated attachment of the electrode at the same electrostimulating region. The structure of the fixation element 105 performs important function in fixing the position of the electrode, as it may use the shape of human body as a fixing element and thus form a shape, which adjusts permanently to the patient and ensure the same conditions for each stimulation.

Another example is a solution of electrostimulating device, which does not comprise the diamagnetic wedge 101, and therefore it is suitable for other applications among those described above, for example, to stimulate the superficially located nerves, to improve the absorption of substances by the skin and to supply the skin with nutrients better. This embodiment uses directly the base of the main magnet 102 adjacent to skin for non-invasive electric connection with tissue. While in the embodiments illustrated in the FIGS. 3 and 4 is the main magnet 102 adapted for non-invasive electrical connection by being provided with the diamagnetic wedge 101 on the side facing the skin, thus on the side located closest to skin, in this embodiment is the main magnet 102 adapted for non-invasive electric connection with the skin on the side facing the skin so that it is provided on its surface with a layer of epoxy resin, conductive plastic or metal, for example nickel, silver, gold or platinum on its surface. Again, this is a bipolar electrode, where the main magnet 102 and the passive conductive contact 104 are fixed in relation to each other in the fixation element 105, which is advantageous for repeated stimulation of a particular place. As in the other exemplary embodiments, it is possible to increase the effects of magnetic field by using the pole piece 103 of the main magnet 102, as it is described above, however, its usage is not necessary for all applications.

The fixation element may be made of plastic, rubber, or any other housing, and for example a neoprene strap, wherein both are glued together or fixed using any other method.

LIST OF REFERENCE SIGNS

1—first electrode pole
2—wiring
3—magnet
4—pole piece
5—fixation element
6—nut
7—adapter
8—second electrode pole
9—source
101—diamagnetic wedge
102—main magnet
103—pole piece
104—passive conductive contact
105—fixation element
106—wiring
107—source

The invention claimed is:

1. An electrostimulation device comprising at least one magnet configured to form a magnetic field, a first electrode pole surrounded by the magnetic field, a fixation element, a current source, a wiring and a second electrode pole, wherein the first electrode pole and the second electrode pole are electrically separated and are adapted on one of their sides for electrical connection with skin of a patient, wherein the first electrode pole and the second electrode pole are further connected by means of wiring to the current source, wherein the at least one magnet is provided with a pole piece.

2. The electrostimulation device according to claim 1, wherein the first electrode pole is arranged inside the at least one magnet with an opening, or the first electrode pole is surrounded by several magnets.

3. The electrostimulation device according to claim 1, wherein the at least one magnet is an electromagnet.

4. The electrostimulation device according to claim 1, wherein the at least one magnet comprises at least two electromagnets configured to direct the magnetic field using different excitation of the at least two electromagnets.

5. The electrostimulation device according to claim 1, wherein the at least one magnet is a permanent magnet.

6. The electrostimulation device according to claim 1, wherein the first electrode pole and the second electrode pole are spaced from each other up to 15 cm.

7. The electrostimulation device according to claim 1, wherein the first electrode pole and the second electrode pole are firmly attached together and thus form one bipolar electrode.

8. The electrostimulation device according to claim 1, wherein the first electrode pole and the second electrode pole are connected by means of wiring to the current source adapted for current settings of 0-50 mA.

9. The electrostimulation device according to claim 8, wherein the current source is adapted for frequency settings of 1-10 Hz.

10. The electrostimulation device according to claim 8, wherein the current source is a source of electric current and is adapted for frequency settings of 50 to 150 Hz.

11. An electrostimulation device comprising:
at least one main magnet configured to form a magnetic field and a passive conductive contact configured to form an electric field,
a fixation element,
a source, and
a wiring,
wherein the passive conductive contact and the at least one main magnet are arranged on the fixation element and isolated from each other, the passive conductive contact is adapted for an electrical connection with skin of a patient with the wiring connected to a current source,
wherein the at least one main magnet is on one side adapted to face the skin of the patient,
wherein the at least one main magnet is adapted for an electrical connection with the skin of the patient and the at least one main magnet is by means of the wiring connected to the current source,
wherein the at least one main magnet is provided with a pole piece,
wherein the at least one main magnet is on the side adapted to face skin of the patient and said at least one magnet is provided with a diamagnetic wedge,
wherein the diamagnetic wedge is arranged so that said diamagnetic wedge is entirely or at least substantially surrounded by the magnetic field from the at least one main magnet,
wherein the diamagnetic wedge is made of material that is both diamagnetic and electrically conductive and the diamagnetic wedge is adapted for an electrical connection with skin of the patient.

12. The electrostimulation device according to claim 11, wherein the at least one main magnet is an electromagnet.

13. The electrostimulation device according to claim 11, wherein the at least one main magnet is made of at least two electromagnets configured to direct the magnetic field by means of different excitation of the at least two electromagnets.

14. The electrostimulation device according to claim 11, wherein the the at least one main magnet is a permanent magnet.

15. The electrostimulation device according to claim 11, wherein the at least one main magnet and the passive conductive contact are spaced from each other up to 15 cm.

16. The electrostimulation device according to claim 11, wherein the at least one main magnet and the passive conductive contact are firmly attached together and thus form one bipolar electrode.

17. The electrostimulation device according to claim 11, wherein the at least one main magnet and the passive conductive contact are connected by means of the wiring to the current source, wherein the current source is a source of electric current and is adapted for current settings of 0 to 50 mA.

18. The electrostimulation device according to claim 11, wherein the current source is a source of electric current and is adapted for frequency settings of 1 to 15 Hz.

* * * * *